United States Patent [19]
Franz et al.

[11] Patent Number: 5,969,199
[45] Date of Patent: Oct. 19, 1999

[54] PROCESS FOR THE ADDITION OF HF TO HALOGENATED ALKENES

[75] Inventors: Raimund Franz, Kelkheim; Günter Siegemund, Hofheim, both of Germany

[73] Assignee: Solvay S.A., Belgium

[*] Notice: This patent is subject to a terminal disclaimer.

[21] Appl. No.: 09/093,534

[22] Filed: Jun. 8, 1998

Related U.S. Application Data

[63] Continuation of application No. 08/723,462, Oct. 9, 1996, Pat. No. 5,847,245, which is a continuation of application No. 08/480,507, Jun. 7, 1995, abandoned, which is a continuation of application No. 08/271,838, Jul. 7, 1994, abandoned.

[30] Foreign Application Priority Data

Jul. 12, 1993 [DE] Germany .............................. 43 23 264
Nov. 19, 1993 [DE] Germany .............................. 43 39 539

[51] Int. Cl.$^6$ .................................................. C07C 19/08
[52] U.S. Cl. .......................... 570/175; 570/164; 570/165
[58] Field of Search ..................... 570/165, 164, 570/175

[56] References Cited

U.S. PATENT DOCUMENTS

| | | |
|---|---|---|
| 3,130,238 | 4/1964 | Tiumae et al. |
| 4,734,526 | 3/1988 | Albert et al. |
| 5,045,634 | 9/1991 | Fernandez et al. |

FOREIGN PATENT DOCUMENTS

| | | |
|---|---|---|
| 1196345 | 11/1985 | Canada . |
| 0 187 643 | 7/1986 | European Pat. Off. . |
| 30 09 760 | 9/1992 | Germany . |
| 902590 | 8/1961 | United Kingdom . |
| 901297 | 7/1992 | United Kingdom . |
| 86/00294 | 1/1986 | WIPO . |

OTHER PUBLICATIONS

Synthetic Methods & Reactions II[1]. (Dec., 1973) pp. 779–780.
Yoneda et al., "Melamine–Hydrogen Fluoride Solution. A Highly Effective and Convenient Hydrofluorination Reagent of Alkenes", Chemistry Letters, Chemical Society of Japan (1983) pp. 1135–1136.
Miller et al., Substitution & Addition Reactions of Fluoroölefins. IV.[1] Reactions of Fluoride Ion with Fluoroölefins[2,3] (Jun. 20, 1960).
Knunyants, "Nucleophilic Addition of Hydrogen Halides to Perfluoroisobutylene", Institute of Heteroorganic Compounds, Academy of Sciences of the USSR Translated from Izvestiya Akademii Nauk SSSR, Seriya Khimocheskaya, No. 4, (1965) pp. 702–704.
Zeifman, et al., "The Chemistry of Perfluoroisobutene", Russian Chemical Reviews, 53 (3), (1984), pp. 256–273.
Aranda, et al., Obtention de fluoroalcools arylaliphatiques par la voie des 'epoxydes et des fluorhydrates d'amines, Bullen De La Societe Chimique de France, (1965) pp. 1890–1892.
Franz, "Ueber Trishydrofluoride Tertiaerer Amine and Ihren Einsatz Als Fluorierungsmittel", Journal of Fluorine Chemistry, 15 (1980) 423–434.
Milos Hudlicky, Chemistry of Organic Flourine Compounds, 2$^{nd}$ Edition (1992) p. 36 et seq.

*Primary Examiner*—Alan Siegel
*Attorney, Agent, or Firm*—Connolly, Bove, Lodge & Hutz, LLP

[57] ABSTRACT

The invention relates to a process for the addition of HF to halogenated alkenes by reacting these with at least one hydrofluoride of the formula [B•n HF], in which B is an organic nitrogen base and n is an integer or fraction $\leq 4$, it being intended that the reaction of perfluoroiso-butene $CF_2=C(CF_3)_2$ is excluded.

32 Claims, No Drawings

PROCESS FOR THE ADDITION OF HF TO HALOGENATED ALKENES

This is a continuation of Ser. No. 08/723,462 filed Oct. 9, 1996 which issued as U.S. Pat. No. 5,847,245, which is a continuation of Ser. No. 08/480,507, filed Jun. 7, 1995 which is now abandoned, which is a continuation of Ser. No. 08/271,838, filed Jul. 7, 1994 which is now abandoned.

DESCRIPTION

Process for the addition of HF to halogenated alkenes

The addition of HF to alkenes has considerable importance for the preparation of fluorine-containing alkanes. This addition, however, frequently cannot be carried out without problems by reaction with liquid or gaseous HF; on the contrary difficulties and complications often occur. The handling of HF is difficult because of its high vapor pressure; at reaction temperatures above its boiling point (19.5° C.) corrosion-resistant pressure vessels are always necessary.

For getting around or minimizing this difficulty the use of polyhydrofluorides of pyridine ("Olah's reagent") as hydrofluorinating agents has been proposed by G. A. Olah et al. (Synthesis 1973, pages 779 to 780). The use of polyhydrofluorides of melamine has a similar aim (N. Yoneda et al., Chemistry Letters 1983, pages 1135 to 1136; 1984, pages 1241 to 1242). These polyhydrofluorides contain 6 to 12 molecules of HF per amine nitrogen atom, but have a distinctly lower vapor pressure than pure hydrogen fluoride.

In comparison with halogen-free alkenes, those double bonds which already carry halogen atoms are distinctly restricted in their reactivity to HF. This is seen e.g. in the fact that polyhydrofluorides such as "Olah's reagent" or melamine polyhydrofluoride do not react with perhalogenated double bonds, in particular perfluorinated double bonds, under the conditions mentioned by the abovementioned authors (see Comparison examples 1 and 2). Instead, the addition of HF in this case must be carried out under drastic conditions using pure HF or alkali metal fluorides. This frequently leads, however, to halogen exchange reactions as an additional complication. Examples of known hydrofluorinations under drastic conditions are the reaction of perhalogenated alkenes with HF on a chromium oxide catalyst at 200 to 500° C., preferably 300 to 400° C., as in GB Patent 901 297, or the reaction of tetrafluoroethene with HF on a chromium oxyfluoride catalyst at temperatures up to 200° C. as in German Offenlegungsschrift 3 009 760. Similarly, the reaction of hexafluoropropene with HF to give 2H-heptafluoropropane at 250 to 450° C. on active carbon is disclosed in GB Patent 902 590.

Even when using water-containing or hydrogen fluoride-containing alkali metal fluorides instead of HF (U.S. Pat. No. 3,130,238, U.S. Pat. No. 5,045,634), the reaction must be carried out at high temperatures and halogen exchange must be expected. In U.S. Pat. No. 5,045,634, a formation of olefin as a result of secondary elimination of hydrogen halide, catalyzed by the basic alkali metal fluoride formed in the reaction, is additionally described. The formation of product mixtures caused by the drastic reaction conditions also makes these processes unsuitable for rationally carrying out a selective addition of HF to halogenated alkenes.

A known method which proceeds under milder conditions is the reaction of trifluorochloroethene $CF_2=CFCl$ with potassium fluoride in formamide to give 1,1,1,2-tetrafluorochloroethane $CF_3$-$CHFCl$ (W. T. Miller et al., JACS 82, pages 3091 to 3099 (1960)). This reaction leads to a conversion of 72% at 55° C. in the course of 30 h. The analogous reaction of hexafluoropropene leads to 2H-heptafluoropropane with a conversion of 60%. The disadvantage of this process of indirect HF addition is that the hydrogen atom needed for this originates from the reaction medium, i.e. the formamide, which leads to undesired by-products.

Perfluoroisobutene $CF_2$-$C(CF_3)_2$ can be hydrofluorinated even at room temperature in the presence of ammonium fluoride using a solution of HF in dioxane (I. L. Knunyants et al., Izvestiya Acad. Nauk USSR, Ser. Chim., 1965, (4), pages 723 to 726; in the English translation pages 702 to 704). The yield according to this literature reference is 88% of theory. Perfluoroisobutene, however, is characterized, compared with other perfluoroalkenes, by an extremely high reactivity (cf. "The Chemistry of Perfluoroisobutene", I. L. Knunyants et al., Uspekhi Khimii 53, pages 431 to 461 (1984), in the English translation: Russian Chemical Reviews 53 (3), pages 256 to 273 (1984)). Correspondingly, a transfer of the reaction route mentioned ($NH_4F$/HF) to other perfluoroalkenes or, generally, haloalkenes is not described in the literature and, as Comparison example 3 shows, is also not possible.

It has now surprisingly been found that the addition of HF to halogenated double bonds, in particular fluorinated double bonds, takes place under very mild conditions with the aid of complex hydrofluorides of organic nitrogen bases which, however, in comparison with the above-mentioned polyhydrofluorides of pyridine ("Olah's reagent") or of melamine, are relatively low in HF.

The present invention thus relates to a process for the addition of HF to a halogenated alkene of the formula (I)

in which $R^1$ to $R^3$ have the following meaning:

$R^1$=F, $CF_3$ or $CF_2R^4$, where $R^4$=$C_1$–$C_4$-alkyl, unsubstituted or substituted by one or more halogen atoms, $R^2$=H, halogen or $CF_3$, $R^3$=H, F, $CF_3$ or $C_1$–$C_4$-alkyl, unsubstituted or substituted by one or more halogen atoms, which comprises reacting a halogenated alkene of the formula (I) with at least one hydrofluoride of an organic nitrogen base of the formula (II)

in which B is an organic nitrogen base and n is an integer or fraction s 4, it being intended that the reaction of perfluoroisobutene $CF_2=C(CF_3)_2$ is excluded.

Preferably the halogenated alkenes of the formula (I) employed are those in which $R^1$=F, $CF_3$ or $C_2F_5$, $R^2$=F, Cl or $CF_3$, and $R^3$=H, F or perfluorinated $C_1$-$C_4$-alkyl.

In particular, the following halogenated alkenes are employed:

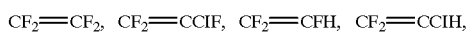

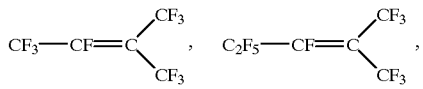

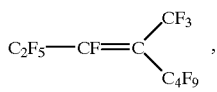

especially, however, $CF_2=CF-CF_3$ (hexafluoropropene).

A mixture of two or more halogenated alkenes of the formula (I) can also be employed in the process according to the invention.

Suitable nitrogen bases B of the formula (II) are amines including nitrogen heterocycles. When the formula given for these amines is the formula (III)

$$R^4R^5R^6N \qquad (III),$$

the radicals $R^4$, $R^5$ and $R^6$ therein can be identical or different and are hydrogen, an alkyl radical having 1 to 20, preferably having 1 to 12, in particular having 1 to 6 carbon atoms, an alkenyl radical having 2 to 20, preferably 2 to 12, in particular 2 to 6 carbon atoms, a cycloalkyl radical having 5 to 7 carbon atoms, a cycloalkenyl radical having 5 to 7 carbon atoms, an aralkyl radical having 7 to 10 carbon atoms or an aryl radical having 6 to 10 carbon atoms which can additionally be substituted by $C_1-C_3$-alkyl or $C_2-C_3$-alkoxy groups.

The alkyl, cycloalkyl, aralkyl and aryl radicals mentioned are preferred here.

In addition, two of the radicals $R^4$ to $R^5$, together with the nitrogen atom carrying them, can form a 5- to 7-membered ring which can contain an oxygen atom or a further nitrogen atom, preferably, however, such a ring contains no oxygen atom and no further nitrogen atom. This ring thus has 5 to 7 members, of which one is the nitrogen atom and the others are preferably $CH_2$ groups. One of the $CH_2$ groups can also be replaced by an oxygen or nitrogen atom, which, however, is not preferred.

Together with the nitrogen atom carrying them, the radicals $R^4$ to $R^6$ can also form two or three 5- to 7-membered, preferably saturated, rings which can contain further nitrogen atoms, such as, for example, in hexamethylenetetramine or diazabicyclooctane.

The nitrogen base B can additionally be a 6-membered heterocyclic ring which can contain one or two nitrogen atoms and can also be benzo-fused, e.g. pyridine, pyrimidine or quinoline.

Particularly preferred organic nitrogen bases B are tertiary amines, including N-heterocycles, having a total of 3 to 12 carbon atoms, especially the following: tri-methylamine, triethylamine, tri-n-propylamine, isopropyl-diethylamine, tri-n-butylamine, N,N,-dimethylaniline, N-methylpiperidine, pyridine, quinoline, N,N'-tetramethylethylenediamine and hexamethylenetetramine.

The number n in the formula (II) is the molar amount of HF per nitrogen atom of the base B and is an integer or fraction $\leq 4$, preferably 0.5 to 3.5, in particular 2 to 3.

In the following, examples of the complex hydrofluorides of the formula (II) which can be employed in the process according to the invention are given:

[$(CH_3)_3N\cdot 2.8$ HF]
[$(C_2H_5)_3N\cdot 2.8$ HF]
[$(n-C_3H_7)_3N\cdot 3.0$ HF]
[$(i-C_3H_7)_2(C_2H_5)N\cdot 2.6$ HF]
[$(n-C_4H_9)_3N\cdot 2.6$ HF]

[$(CH_3)_2N-CH_2-CH_2-N(CH_3)_2\cdot 4.7$]

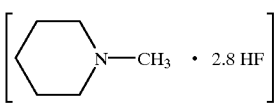

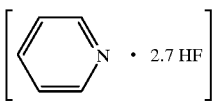

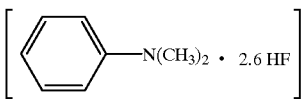

[$(CH_2)_6N_4\cdot 2$ HF]

These hydrofluorides are known from the literature, e.g. from Bulletin Soc. Chim. France 1965, pages 1890 to 1892 or from J. Fluorine Chemistry 15 (1980), pages 423 to 434. in the molar composition given, they are stable complexes which, in contrast to amine hydrofluorides having a higher hydrogen fluoride content (n>4), such as e.g. [pyridine•9 HF], i.e. "Olah's reagent", exhibit no HF vapor pressure and are therefore considerably simpler to handle and in some cases can even be distilled in equipment made of borosilicate glass. In the process according to the invention, the use of [triethylamine•2.8 HF] or [tributylamine•2.6 HF] is particularly preferred.

The hydrofluoride of the formula (II) to be employed in the process according to the invention can be prepared by direct reaction of the amines with HF. In particular from the background of the facts verified below in Comparison examples 1, 2 and 4 that "Olah's reagent" and other amine hydrofluorides having more than 4 HF molecules per amine nitrogen atom are not able to hydrofluorinate a perhalogenated olefinic double bond, it was an extremely surprising finding that the hydrofluorides to be employed in the process according to the invention, which are comparatively low in HF, react very easily.

The process according to the invention can be carried out in a closed pressure vessel or at atmospheric pressure. If the reaction is carried out batchwise and the boiling points of substrate and product are low, a stirred autoclave is expediently selected in which the reaction can proceed under autogenous pressure. In this case, the progress of the reaction is as a rule recognizable by the decrease in the internal pressure. If the boiling points are sufficiently high, a stirred flask, optionally with a reflux condenser, can be used. After the end of the reaction the amount of HF consumed can be replaced again in a suitable manner, e.g. by passing in, condensing in or pumping in HF, and a further reaction can follow.

If it is intended to carry out the reaction without pressure in spite of low boiling points, the residence time of the substrate in the liquid hydrofluoride needed for reaction can be realized by means of a gas circulation. The addition of the HF can in this case also be carried out simultaneously with the addition of the substrate. In this case, it is preferred to carry out the process continuously in a bubble column which can consist of corrosion-resistant metal, borosilicate glass or synthetic material. The reaction temperatures which can be used in the process according to the invention depend on the halogenated alkene employed and in general are −10 to +200° C. The reaction is preferably carried out above the melting point of the hydrofluoride selected, i.e. in the homogeneous liquid phase, preferably at 0 to +100° C., particularly preferably at +20 to +80° C.

In general, addition of solvent is unnecessary; if required, however, the reaction can be carried out in the presence of adequate amounts of an aprotic polar solvent such as dioxane, tetrahydrofuran, acetonitrile or N-methylpyrrolidone.

The hydrofluorination product is isolated by distillation or (when using a pressure vessel) by releasing the pressure and condensing. It is a particular advantage of the process according to the invention that the hydrofluorination products thus prepared are free of impurities whose formation interferes in other preparation processes which proceed at high temperatures.

The following examples illustrate the process according to the invention. The percentages are percentages by weight, if not stated otherwise.

COMPARISON EXAMPLE 1

Analogously to a procedure given by G. A. Olah et al., (Synthesis 1973, pages 779 to 783), 100 g (0.39 mol) of the hydrofluoride [pyridine•9 HF], i.e. "Olah's reagent", were introduced into a 500 ml stirred autoclave made of V4A steel and 80 g of hexafluoropropene (0.53 mol) were injected from a pressure storage reservoir. The autoclave contents were heated to 50 to 51° C. with stirring and kept at this temperature for 24 h; during the heating period the internal pressure rose from 6 to 8.8 bar and did not change any more. The autoclave contents were then condensed, if gaseous, in a trap cooled with dry ice and analyzed. A measurable content of 2H-heptafluoropropane could not be determined.

COMPARISON EXAMPLE 2

Analogously to a procedure of N. Yoneda et al. (Chemistry Letters 1983, pages 1135 to 1136), 160 g of a 24 percent solution of melamine (2,4,6-triaminotriazine) in anhydrous hydrogen fluoride (this corresponds to [melamine•20 HF]) were introduced into a 500 ml stirred autoclave made of V4A steel and 220 g of hexafluoropropene (about 1.5 mol) were injected from a pressure storage bottle. The autoclave contents were heated to 52° C. with stirring and kept at this temperature. After an experimental period of 20 h, investigations of a gas sample by nuclear magnetic resonance spectroscopy did not show any conversion at all. After this, the internal temperature of the autoclave was increased from 52° C. to about 100° C. and after a further 20 h a sample was removed and analyzed as described. The spectrum did not show any measurable conversion to 2H-heptafluoropropane.

COMPARISON EXAMPLE 3

Analogously to the reaction of perfluoroisobutene with hydrogen fluoride in the presence of ammonium fluoride in dioxane described in Izvestiya Acad. Nauk USSR, Ser. Chim., 1965, (4), pages 723 to 726 (in the English translation pages 702 to 704), a reaction of hexafluoropropene (instead of perfluoroisobutene) was now attempted.

150 g of anhydrous dioxane were introduced into a stirred vessel made of polyethylene and cooled in an ice bath, and 45 g of hydrogen fluoride (2.25 mol) were added. 3 g of ammonium fluoride were introduced into a 500 ml autoclave having a magnetic lift stirrer, the solution of HF in dioxane was sucked into the then closed autoclave and 33 g of hexafluoropropene (0.22 mol) were injected. The reaction mixture was stirred at room temperature for a total of 90 h. In the time interval from 5 to 10 hours, gas samples were in each case taken for IR and NMR analyses. Even after 90 h, no 2H-heptafluoropropane could be detected in the reaction mixture. After releasing the pressure and opening the reactor, in addition to unchanged starting substance dark-colored resinification products dissolved in dioxane were found.

COMPARISON EXAMPLE 4

126 g of a hydrofluoride of the composition [(n-$C_4H_9$)$_3$N•6.6 HF] were introduced into a 500 ml stirred autoclave made of V4A steel and 70 g of trifluorochloroethene (0.6 mol) were injected from a pressure storage bottle. The reaction mixture was stirred under autogenous pressure at 30° C. for 1.5 h, then at about 60° C. for 2 h and finally at 80° C. for 15 h; no pressure decrease was observed in this case. The $^{19}$F-NMR spectrum of a sample taken after this showed no conversion to 1,1,1,2-tetra-fluorochloroethane.

COMPARISON EXAMPLE 5

90 g of a hydrofluoride of the composition [(n-$C_4H_9$)$_3$N 4.6 HF] were introduced into a gas-washing bottle provided with a ceramic frit, and 40 g of hexafluoropropene were passed through at 80° C. and condensed in a trap cooled with dry ice. The condensate was passed through the liquid hydrofluoride a further time and again condensed. The IR spectrum of a sample indicated the presence of pure hexafluoropropene; the same was the case after passing the same substrate through said hydrofluoride a total of 4 times.

EXAMPLE 1

1900 g (8.0 mol) of [n-$C_4H_9$)$_3$N•2.6 HF] were introduced into a 5-liter stirred autoclave and 600 g of hexafluoropropene (4.0 mol) were pumped in from a storage reservoir with stirring at 25 to 35° C. The autoclave was then heated to 75° C. and after reaching this temperature the pressure was released through a trap cooled with dry ice. The contents of this trap (660 g) consisted according to the infrared and the $^1$H- and $^{19}$F-NMR spectra to 97% of 2H-heptafluoropropane and to about 3% of hexafluoropropene. The composition of the autoclave residue was then determined by titration of a carefully degassed sample with alkali solution. n was calculated to be 2.1, thus 0.5×8=4.0 mol of hydrogen fluoride had been consumed, which were then replaced by pumping in from a storage reservoir. The process was then repeated by pumping in 600 g (4.0 mol) of hexafluoropropene. A 2nd repetition followed. The crude 2H-heptafluoropropane of boiling point −18° C. was then freed from unreacted hexafluoropropene by fractional distillation (b.p. −27° C.).

EXAMPLE 2

157 g (1.0 mol) of [($C_2H_5$)$_3$N•2.8 EF] were introduced into a 500 ml stirred flask made of borosilicate glass, which was provided with a reflux condenser charged with dry ice and with a thermometer for measuring the reflux temperature, and 15 g of hexafluoropropene (0.1 mol) were passed in from a pressure storage reservoir. With stirring, vigorous reflux commenced at once and was maintained by gentle heating of the flask. The reflux temperature rose from initially −27° C. to −18° C. within a short time and then remained constant. The gaseous product was then removed via a tap attached below the reflux condenser and condensed in a cold trap. According to the 3H- and $^{19}$F-NMR spectra, this product consisted to 95% to 2H-heptafluoropropane and to about 5% of hexafluoropropene. The introduction of hexafluoropropene and the removal of 2H-heptafluoropropane was repeated four times.

COMPARISON EXAMPLE 6

This experiment was carried out analogously to Example 2, with the difference, however, that the HF content in the triethylamine hydrofluoride was much higher. 280 g of a solution of the composition [$(C_2H_5)_3N \cdot 23$ HF] in an apparatus of capacity 500 ml made of polytetrafluoroethylene were used. Even after refluxing hexafluoropropene for 5 hours, still no rise in the boiling point, and thus also no indication of 2H-heptafluoropropane, could be found.

EXAMPLE 3

For this experiment, a 500 ml reaction flask made of borosilicate glass was used in which a frit was incorporated for the finely distributed introduction of hexafluoropropene. The flask was connected by means of a tube to the still of an apparatus for fractional distillation whose take-off valve for gaseous distillate was in turn connected to the frit in the reaction flask via a gas diaphragm pump so that a gas circulation was achieved. 237 g (1.0 mol) of [$(n-C_4H_9)_3N \cdot 2.6$ HF] were then introduced into the reaction flask. By means of a T-piece attached in front of the frit, 150 g (1.0 mol) of hexafluoropropene were passed in from a pressure storage reservoir in the course of 2 h and after onset of reflux in the distillation apparatus (−27° C.) the gas circulation was set going by switching on the diaphragm pump. This was also maintained after the end of hexafluoropropene introduction. In the course of 3 h, 146 g of a boiling product whose temperature rose in the course of the reaction period from −27° C. to −18° C. collected in the still of the distillation apparatus. This product was then removed and analyzed. According to the $^{19}$F-NMR spectrum, it consisted to 90% of 2H-heptafluoropropane and to about 10% of unreacted hexafluoropropene.

EXAMPLE 4

A bubble column made of borosilicate glass of internal diameter 22 mm and length 1800 mm which could be heated from outside by warm water was filled with the hydrofluoride [$(n-C_4H_9)_3N \cdot 2.6$ HF]. At an internal temperature of 75° C., hexafluoropropene was passed in at a rate of 15 g/h through a frit attached at the foot of the column. The 2H-heptafluoropropane emerging at the head of the bubble column was condensed in a cold trap and identified by means of IR, $^{19}$F-NMR and $^1$H-NMR spectra. The experimental period was 4 hours. The gas-chromatographic analysis of this crude product showed a content of 98.4% of 2H-heptafluoropropane and about 1.5% of hexafluoropropene.

EXAMPLE 5

The liquid amine hydrofluoride was circulated in the bubble column described in Example 4 by means of hose connections and a peristaltic pump. Into this liquid circulation was incorporated a stirred vessel made of polyethylene in which the consumed hydrogen fluoride was replaced by weight-controlled absorption from a storage vessel. The crude product expelled was free of traces of HF and had a content of almost 99% of 2H-heptafluoropropane and about 1% of hexafluoropropene.

EXAMPLE 6

78.5 g (0.5 mol) of the hydrofluoride [$(C_2H_5)_3N \cdot 2.8$ HF] were introduced into a 500 ml stirred autoclave made of V4A steel and 160 g of hexafluoropropene, (1.07 mol) were injected from a pressure storage reservoir. The autoclave contents were heated to 50° C. and stirred under autogenous pressure. The internal pressure of initially 10 bar decreased even during heating to one half and almost completely disappeared in the course of a further 4 hours. The pressure of the autoclave contents was then released through a washing bottle containing 2N hydrochloric acid (for the absorption of triethylamine) and a drying tower containing anhydrous calcium chloride, and the 2H-heptafluoropropane was condensed in a trap cooled with dry ice. The crude product thus obtained was investigated by gas chromatography and also by means of GC-MS. In addition to 96.2% of the desired 2H-heptafluoropropane, it contained about 3.5% of hexafluoropropene. A trace analysis for the determination of the highly toxic perfluoroisobutene showed no measurable content (<1 ppb).

COMPARISON EXAMPLE 7 a) 105 g of a solution of the composition [$(C_2H_5)_3N \cdot 24$ HF] were introduced into the autoclave described in Example 6, 30 g of hexafluoropropene were injected from a pressure storage bottle and the autoclave contents were heated to 55° C. After stirring at this temperature for one hour, the $^{19}$F-spectrum of a gas sample indicated no measurable conversion to 2H-heptafluoropropane.

b) A mixture, as described in a), was first stirred at 90° C. for 1 h, then at 50° C. for a further 42 h, under autogenous pressure. A sample removed after this was analyzed. The $^{19}$F-NMR spectrum again indicated no measurable conversion to 2H-heptafluoropropane.

EXAMPLE 7

40 g of tri-n-butylamine were introduced into a stirred vessel made of polyethylene. The lid of the vessel was connected via hose lines to a storage reservoir for hexafluoropropene (standing on a balance), to a stirred evaporator vessel which contained 20 g (1 mol) of hydrogen fluoride, and to a trap cooled with dry ice. Hexafluoropropene and— by means of a dry stream of nitrogen blown into the evaporator—hydrogen fluoride gas were then passed into the tributylamine such that the 20 g of hydrogen fluoride contained in the evaporator were consumed in the same time as 150 g (1 mol) of hexafluoropropene. The contents of the cold trap were recondensed by means of a tube filled with calcium chloride and thus freed from accompanying hydrogen fluoride. in spite of the low molar amount of hydrogen fluoride per amine molecule and in spite of the extremely short residence time of the hexafluoropropene in the reaction medium, the gas-chromatographic analysis showed a content of 14% of 2H-heptafluoropropane in addition to about 86% of hexafluoropropene.

EXAMPLE 8

118.5 g (0.5 mol) of the hydrofluoride [tri-n-butylamine •2.6 HF] were introduced into a 500 ml stirred autoclave made of stainless steel, 58 g of trifluorochloroethene $CF_2$=CClF (0.5 mol) were injected from a pressure storage reservoir and the mixture was stirred at 65° C. The internal pressure decreased from 6 bar to less than 1 bar in the course of 24 h. The pressure of the autoclave was released via a cold trap cooled with dry ice and the product (crude yield 61 g, 90% of theory) was identified as 1,1,1,2-tetrafluorochloroethane (R 124) by means of the $^1$H- and $^{19}$F-NMR spectra.

EXAMPLE 9

At an internal temperature of 57° C., 1.5 liters of gaseous trifluorochloroethene were introduced through a frit into an externally heatable bubble column made of borosilicate glass of cross section 22 mm, which was filled to a height of 1.5 m with the liquid hydrofluoride [(n-C$_4$H$_9$)$_3$N•2.4 HF], and circulated by means of a pump through a buffer vessel of volume about 1 liter. The circulation rate of the gas was adjusted such that a good distribution of the gas bubbles in the medium was achieved (5 to 8 l/h); the residence time of the bubbles in the medium during each passage was about 10 sec. After an effective total residence time of the gas in the medium of 3.5 min, the chromatogram of the recirculating gas (conditions: 5 m-long +e,fra /14+ee " column of ®Porasil C, containing 5% of oxydipropionitrile, heat conductivity detection, temperature 80° C. isothermal) showed a conversion of 50% to a product which was identified as 1,1,1,2-tetrafluorochloroethane (R 124) by means of $^1$H- and $^{19}$F-NMR spectra.

EXAMPLE 10

At an internal temperature of 55° C., 1.5 liters of gaseous tetrafluoroethene were introduced through a frit into an externally heatable bubble column made of borosilicate glass of cross section 22 mm, which was filled to a height of 1.5 m with the liquid hydrofluoride [(n-C$_4$H$_9$)$_3$N•2.4 HF], and circulated by means of a pump through a buffer vessel of volume about 1 liter. The circulation rate of the gas was adjusted such that a good distribution of the gas bubbles in the medium was achieved (5 to 8 l/h); the residence time of the bubbles in the medium during each passage was about 10 seconds. After an effective total residence time of the gas in the medium of 3 minutes, the chromatogram of the circulating gas (conditions as in Example 9) showed a conversion of 97% to a product which was identified as pentafluoroethane (R 125) by comparison with an authentic sample, and also—after condensing out the mixture—by means of H- and $^{19}$F-NMR spectra.

EXAMPLE 11

50 g (0.21 mol) of the hydrofluoride [(n-C$_4$H$_9$)$_3$N•2.6 HF] were introduced into a stirred autoclave of capacity 125 ml and 10 g (0.1 mol) of 1,1-difluorochloroethene (R 1122) were injected from a pressure storage bottle. The autoclave contents were then stirred under autogenous pressure at 65° C. for 22 h and at 82° C. for a further 46 h. The volatile components of the reaction mixture were then collected in a cold trap and analyzed. According to a gas chromatogram (conditions as in Example 9), in addition to trifluorochloroethene they contained a fraction of 12%, which was identified as 1,1,1-trifluorochloroethane (R 133a) by means of $^1$H- and $^{19}$F-nuclear magnetic resonance spectra.

EXAMPLE 12

30 g (0.13 mol) of the hydrofluoride [(n-C$_4$H$_9$)$_3$N•2.6 HF] were introduced into a stirred autoclave of capacity 125 ml and 11 g (0.06 mol) of 2H-heptafluoro-2-butene were injected from a pressure storage bottle. The reaction mixture was stirred at 65° C. until the internal pressure had fallen from initially 3 bar to 1 bar. The gas chromatogram of the volatile components of the autoclave contents recorded after this (conditions as in Example 9) showed that 99% of a substance was contained which was identified as 2,2-dihydrooctafluorobutane by $^1$H- and $^{19}$F-nuclear magnetic resonance spectra.

EXAMPLE 13

79 g (about 0.5 mol) of the liquid hydrofluoride [(n-C$_2$H$_5$)$_3$N•2.8 HF] were introduced into a stirred flask made of borosilicate glass and 150 g of perfluoro(2-methylpent-2-ene) (0.5 mol) were added at 25° C. from a dropping funnel. 250 ml of water were then added, and the organic phase was separated off (yield 155 g) and dried over magnesium sulfate. According to the gas chromatogram, it consisted to 96.1% of a product which was identified as 2H-perfluoro(2-methylpentane) by means of $^1$H- and $^{19}$F-nuclear magnetic resonance spectra.

EXAMPLE 14

120 g (about 0.5 mol) of the liquid hydrofluoride [(n-C$_4$H$_9$)$_3$N•2.6 HF] were introduced into a 500 ml stirred flask made of borosilicate glass and 150 g of perfluoro(2-methylbut-2-ene) (0.5 mol) were added at 25° C. from a dropping funnel. The homogeneous reaction mixture was then distilled. 150 g of a product of boiling point 60 to 61° C. were obtained, which was identified as 2H-perfluoro(2-methylpentane) by means of $^1$H- and $^{19}$F-NMR spectra.

EXAMPLE 15

72.5 g (0.5 mol) of the hydrofluoride [piperidine•2.9 HF] were introduced into a stirred autoclave of capacity 300 ml and 30 g of hexafluoropropene (0.2 mol) were injected from a pressure storage reservoir. The reaction mixture was stirred at 60° C. for 24 h. The gas chromatogram of the volatile components of the reactor contents recorded after this indicated a content of 88.7% of 2H-heptafluoropropane in addition to 11.1% of unreacted hexafluoropropene.

EXAMPLE 16

71 g (0.5 mol) of the hydrofluoride [morpholine•2.8 HF] were introduced into a stirred autoclave of capacity 300 ml and 30 g (0.2 mol) of hexafluoropropene were injected from a pressure storage reservoir. The reaction mixture was stirred at 60° C. for 24 h. The gas chromatogram of the volatile components of the autoclave contents recorded after this indicated a content of 25% of 2H-heptafluoropropane in addition to about 70% of unreacted hexafluoropropene.

EXAMPLE 17

65 g (0.5 mol) of the hydrofluoride [t-butylamine 2.8 HF] were introduced into a stirred autoclave of capacity 300 ml and 26 g (0.17 mol) of hexafluoropropene were injected from a pressure storage reservoir. The reaction mixture was stirred at 60° C. for 24 h. The gas chromatogram of the volatile components of the autoclave contents recorded after this indicated a content of 26% of 2H-heptafluoropropane in addition to 74% of unreacted hexafluoropropene.

We claim:

1. A process for the addition of HF to a halogenated alkene of the formula (I)

$$R^1CF=CR^2R^3 \tag{I}$$

in which $R^1$ to $R^3$ have the following meaning:

$R^1$=F, CF$_3$ or CF$_2$R$^4$, where R$^4$=C$_1$–C$_4$-alkyl, unsubstituted or substituted by one or more halogen atoms, $R^2$=H, halogen or CF$_3$, $R^3$=H, F, CF$_3$ or C$_1$–C$_4$-alkyl, unsubstituted or substituted by one or more halogen atoms, which comprises (a) preparing at least one hydrofluoride of an organic nitrogen base of the formula (II)

$$\{B•n\ HF\} \tag{II}$$

in which B is an organic nitrogen base and n is an integer or fraction ≦4, by reaction of the organic base B with HF; and (b) reacting the halogenated alkene of the formula (I) with said hydrofluoride, wherein formula (I) is not $CF_2=C(CF_3)_2$.

2. The process as claimed in claim 1, wherein a halogenated alkene of the formula (I) is employed, in which:

$R^1$=F, $CF_3$ or $C_2F_5$, $R^2$=F, Cl or $CF_3$, and $R^3$ =H, F or perfluorinated $C_1$–$C_4$-alkyl.

3. The process as claimed in claim 1, wherein the halogenated alkene of the formula (I) employed is

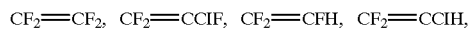

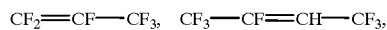

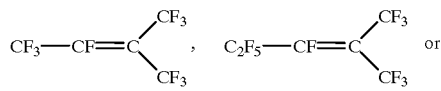

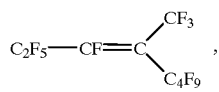

4. The process as claimed in claim 1, wherein the halogenated alkene of the formula (I) employed is $CF_2$=CF-$CF_3$ (hexafluoropropene).

5. The process as claimed in claim 1, wherein n in the formula (II) is an integer or fraction from 0.5 to 3.5.

6. The process as claimed in claim 1, wherein n in the formula (II) is an integer or fraction from 2 to 3.

7. The process as claimed in claim 1, wherein B is an organic nitrogen base of the formula (III) $R^4R^5R^6N$, in which the radicals $R^4$ to $R^6$ are identical or different and each of these radicals is hydrogen, an alkyl radical having 1 to 20 carbon atoms, an alkenyl radical having 2 to 20 carbon atoms, a cycloalkyl radical having 5 to 7 carbon atoms, a cycloalkenyl radical having 5 to 7 carbon atoms, an aralkyl radical having 7 to 10 carbon atoms or an aryl radical having 6 to 10 carbon atoms, which can additionally be substituted by $C_1$–$C_3$-alkyl or $C_1$–$C_3$-alkoxy radicals, or in which two of the radicals $R^4$ to $R^6$, together with the nitrogen atom carrying them, form a 5- to 7-membered ring which can contain an oxygen or a further nitrogen atom, or in which the radicals $R^4$ to $R^6$, together with the nitrogen atom carrying them, form two or three 5- to 7-membered rings which can contain further nitrogen atoms.

8. The process as claimed in claim 1, wherein B is an organic nitrogen base of the formula (III) $R^4R^5R^6N$, in which the radicals $R^4$ to $R^6$ are identical or different and each of these radicals is an alkyl radical having 1 to 20 carbon atoms, a cycloalkyl radical having 1 to 7 carbon atoms, an aralkyl radical having 7 to 10 carbon atoms or an aryl radical having 6 to 10 carbon atoms, which can additionally be substituted by $C_1$–$C_3$-alkyl or $C_1$–$C_3$-alkoxy radicals, or in which two of the radicals $R^4$ to R6, together with the nitrogen atom carrying them, form a 5- to 7-membered ring which can contain an oxygen or a further nitrogen atom, or in which the radicals $R^4$ to $R^6$, together with the nitrogen atom carrying them, form two or three 5- to 7-membered rings which can contain further nitrogen atoms.

9. The process as claimed in claim 7, wherein at least one of the radicals $R^4$ to $R^6$ is an alkyl radical having 1 to 12 carbon atoms.

10. The process as claimed in claim 7, wherein at least one of the radicals $R^4$ to $R^6$ is an alkyl radical having 1 to 6 carbon atoms.

11. The process as claimed in claim 1, wherein the organic nitrogen base B is tertiary and has a total of 3 to 12 carbon atoms.

12. The process as claimed in claim 1, wherein the organic nitrogen base B is a 6-membered heterocyclic ring which contains 1 or 2 nitrogen atoms and can also be benzo-fused.

13. The process as claimed in claim 1, wherein the organic nitrogen base B is a trialkylamine having 3 to 12 carbon atoms.

14. The process as claimed in claim 1, wherein the reaction is carried out at a temperature from 0 to 100° C.

15. The process as claimed in claim 1, wherein the reaction is carried out at a temperature from 20 to 80° C.

16. The process as claimed in claim 1, wherein the reaction is carried out in a bubble column.

17. The process as claimed in claim 1, wherein the reaction is carried out in a pressure vessel.

18. The process as claimed in claim 17, wherein the process is carried out batchwise.

19. The process as claimed in claim 1, wherein the process is carried out batchwise.

20. The process as claimed in claim 19 wherein after the end of the reaction the amount of HF consumed is replaced to reform said hydrofluoride.

21. The process as claimed in claim 18, wherein after the end of the reaction the amount of HF consumed is replaced to reform said hydrofluoride.

22. The process as claimed in claim 16, wherein said process is carried out continuously.

23. The process as claimed in claim 1, wherein said process is carried out continuously.

24. The process as claimed in claim 22, in which the consumed hydrogen fluoride is replaced to reform said hydrofluoride.

25. The process as claimed in claim 23, in which the consumed hydrogen fluoride is replaced to reform said hydrofluoride.

26. The process as claimed in claim 1, wherein n is an integer or fraction ≦3.5.

27. The process as claimed in claim 1, wherein n is an integer or fraction ≦3.

28. A process for the hydrofluorination of a halogenated alkene wherein said halogenated alkene is

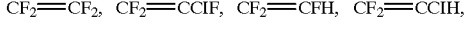

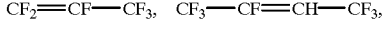

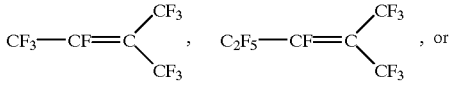

-continued

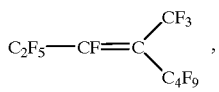

said process comprising:
(a) hydrofluorinating said halogenated alkene essentially by reaction with at least one hydrofluoride of an organic nitrogen base of the formula (II)

{B·nHF}  (II)

in which B is a tertiary organic nitrogen base having a total of 3 to 12 carbon atoms and n is a number $\leq 4$, and
(b) isolating essentially only the hydrofluorinated addition product having the halogen atoms of said halogenated alkene and, in addition, an additional F atom and an additional H atom.

29. The process as claimed in claim 28, wherein n is an integer or fraction $\leq 3.5$.

30. The process as claimed in claim 28, wherein n is an integer or fraction $\leq 3$.

31. A process for the addition of HF to a halogenated alkene of the formula (I)

$R^1CF=CR^2R^3$  (I)

in which $R^1$ to $R^3$ have the following meaning:

$R^1$=F, $CF_3$ or $CF_2R^4$, where $R^4$=$C_1$–$C_4$-alkyl, unsubstituted or substituted by one or more halogen atoms, $R^2$=H, halogen or $CF_3$, $R^3$=H, F, $CF_3$ or $C_1$–$C_4$-alkyl, unsubstituted or substituted by one or more halogen atoms, which comprises (a) preparing at least one hydrofluoride of an organic nitrogen base of the formula (II)

{B·n HF}  (II)

in which B is an organic nitrogen base and n is an integer or fraction $\leq 4$, by reaction of the organic base B with HF; and (b) reacting the halogenated alkene of the formula (I) in the substantial absence of free hydrogen fluoride with said hydrofluoride, wherein formula (I) is not $CF_2=C(CF_3)_2$.

32. The process as claimed in claim 1, wherein the hydrofluoride is prepared by the reaction of hydrogen fluoride with said organic nitrogen base in an amount so that n does not exceed 4.

* * * * *